(12) United States Patent
Zhang

(10) Patent No.: US 8,210,053 B2
(45) Date of Patent: Jul. 3, 2012

(54) APPARATUS FOR TESTING OBJECT STRENGTH

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 383 days.

(21) Appl. No.: 12/635,671

(22) Filed: Dec. 10, 2009

(65) Prior Publication Data

US 2010/0307261 A1 Dec. 9, 2010

(30) Foreign Application Priority Data

Jun. 5, 2009 (CN) .......................... 2009 1 0302965

(51) Int. Cl.
*G01N 3/00* (2006.01)
(52) U.S. Cl. .......................................................... 73/838
(58) Field of Classification Search .................... 73/838
See application file for complete search history.

(56) References Cited

U.S. PATENT DOCUMENTS 4,055,992 A * 11/1977 Pizzarello ........................ 73/791
6,228,000 B1 * 5/2001 Jones ................................ 482/8

* cited by examiner

*Primary Examiner* — Harshad Patel
*Assistant Examiner* — Octavia Davis-Hollington
(74) *Attorney, Agent, or Firm* — Altis Law Group, Inc.

(57) ABSTRACT

An apparatus for testing object strength includes a support platform, a force gauge for reading push or pull force exerted on an object, an installation mechanism for slidable installation of the force gauge on the support platform, an installation board supporting the object, a pull-push mechanism connected to the force gauge to be pushed or pulled by the force gauge and exert force on the object, and an adjustment mechanism. The adjustment mechanism includes a pedestal secured to the support platform, a slider slidably mounted to the pedestal, an adjustment rod pivotally mounted to the pedestal and threaded into the slider, and a manipulation member fixed to the adjustment rod. The manipulation member rotates the adjustment rod relative to the slider. Thus the slider slides relative to the pedestal. The installation board adjusts the object relative to the support platform.

10 Claims, 4 Drawing Sheets

APPARATUS FOR TESTING OBJECT STRENGTH

CROSS-REFERENCES TO RELATED APPLICATION

A relevant subject matter is disclosed in the co-pending U.S. patent application Ser. No. 12/551,444 filed on Aug. 31, 2009, and entitled "APPARATUS FOR TESTING STRENGTH OF OBJECTS", and a co-pending U.S. patent application Ser. No. 12/635,667 entitled "APPARATUS FOR TESTING OBJECT STRENGTH" filed at the same date as this patent application, which are assigned to the same assignee as this patent application.

BACKGROUND

1. Technical Field

The disclosure relates to apparatuses for testing object strength, and particularly, to an apparatus for testing strength of molded products.

2. Description of Related Art

Typically, corners of an injection molded product are formed by influx of two or more streams of molten material. As a result, the corners may not bind well, presenting relative weakness of the seal therebetween. Consequently, a risk of rupture is present.

In practice, there is a need to test the strength of injection molded products at corners. Typically, the sides near the corners of the products are pulled manually to test the rupture strength. However, the manual test is not accurate and inefficient.

DETAILED DESCRIPTION

Figure 1:
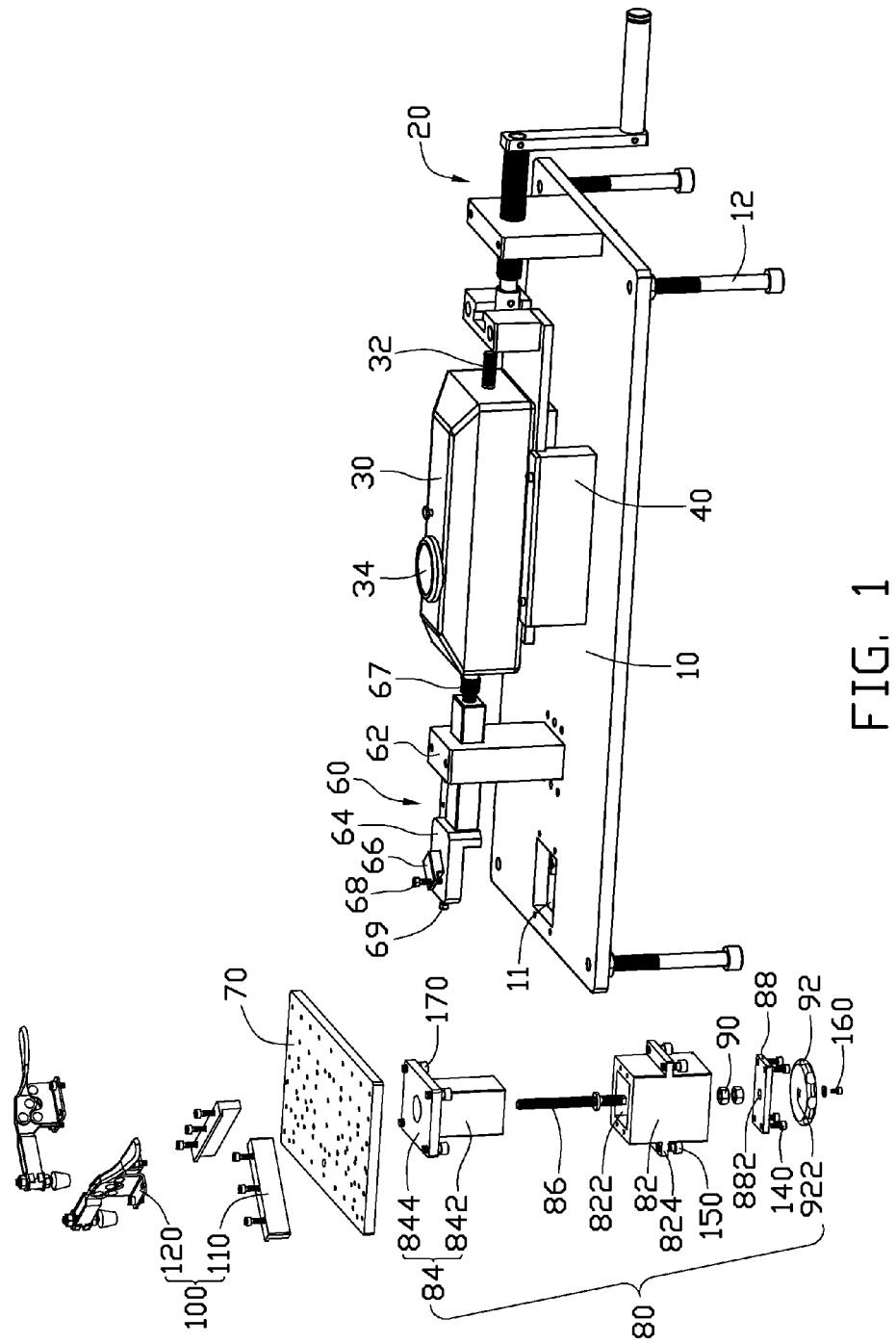
FIG. 1 is an exploded, isometric view showing an exemplary embodiment of an apparatus for testing object strength.

Referring to FIG. 1, an exemplary embodiment of an apparatus for testing object strength includes a rectangular support platform 10, a plurality of support bolts 12 under the support platform 10, a force gauge 30, an installation mechanism 40 for slidable installation of the force gauge 30 on the support platform 10, a drive mechanism 20 mounted to the support platform 10 to move the force gauge 30, a push-pull mechanism 60 for exerting push or pull force on the object, an installation board 70 for supporting the object, an adjustment mechanism 80 for adjusting the installation board 70 up and down, and a clamping mechanism 100 which can be placed at different positions on the installation board 70.

A rectangular opening 11 is defined in the support platform 10 adjacent to an end thereof.

Figure 2:
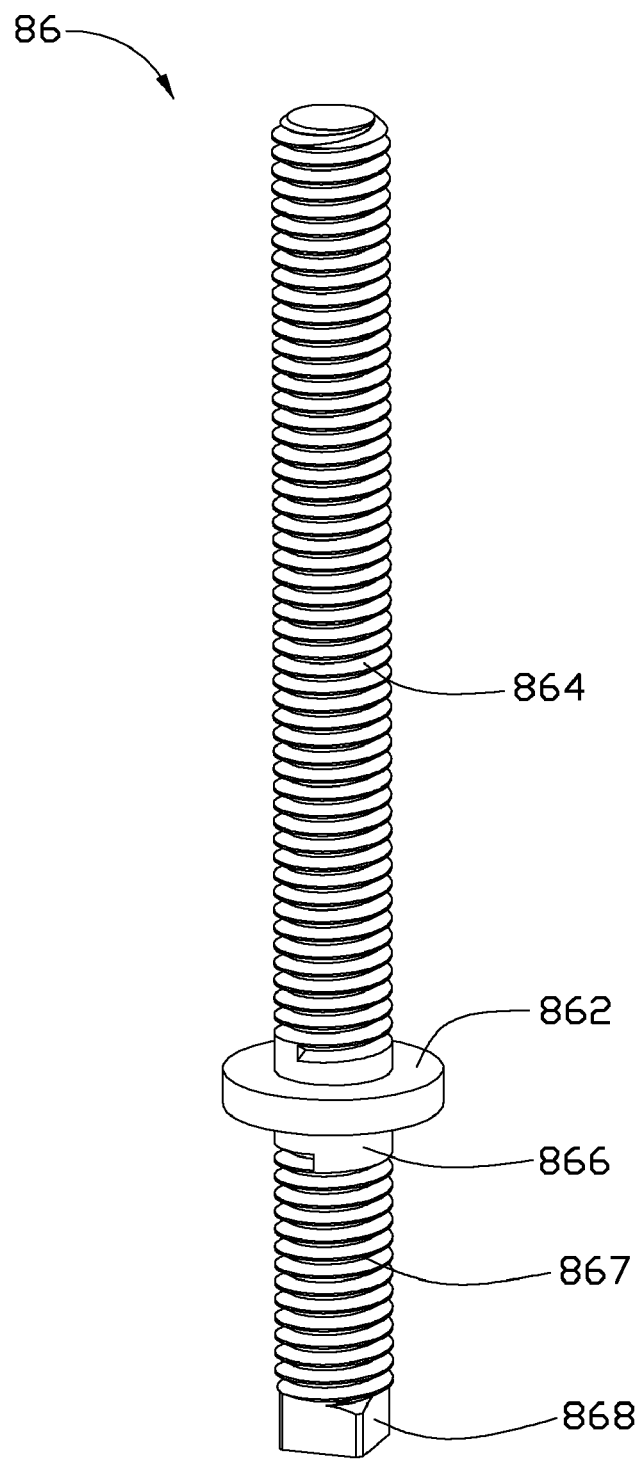
FIG. 2 is an enlarged, isometric view of an adjustment rod of the apparatus of FIG. 1.

Referring to FIG. 2, the adjustment mechanism 80 includes a pedestal 82 received in the opening 11 of the support platform 10, a slider 84, an adjustment rod 86, a mounting panel 88, two circular fasteners 90, and a manipulation member 92. A rectangular chamber 822 is defined between a top surface and a bottom surface of the pedestal 82 and extends along the lengthwise direction of the pedestal 82. Two bulges 824 protrude from two opposite lateral surfaces of the pedestal 82. The slider 84 includes an elongated sliding block 842 slidably received in the chamber 822 of the pedestal 82, and a carrier 844 formed on top of the sliding block 842. The cross-section of the carrier 844 is larger than that of the sliding block 842. A threaded hole 846 (see FIG. 4) is defined in the underside of the sliding block 842 and extends along the lengthwise direction of the sliding block 842. The adjustment rod 86 includes a round flange 862 formed on the middle thereof, a first threaded section 864 extending out from a side of the flange 862, a smooth section 866, a second threaded section 867 corresponding to the circular fasteners 90, and a rectangular fixing section 868. The smooth section 866, the second threaded section 867, and the fixing section 868 are serially formed on an opposite side of the flange 862. A fixing hole 869 (see FIG. 4) is defined in the distal end of the fixing section 868. A smooth hole 882 is defined in the mounting panel 88 corresponding to the section 866 of the adjustment rod 86. The manipulation member 92 has a shape of a round tray. A securing hole 922 is defined in the center of the manipulation member 92.

The clamping mechanism 100 includes two blocking portions 110 and two clamps 120, all of which are installed on the top of the installation board 70.

The force gauge 30 includes two threaded fasteners 32 extending from two opposite ends thereof, and a dial 34 on the top thereof.

The push-pull mechanism 60 includes a stand portion 62 fixed at different positions on the support platform 10, a sliding portion 64 slidably extending through the stand portion 62, a drive portion 66 adjustably mounted to one end of the sliding portion 64, and a connecting portion 67 connecting the other end of the sliding portion 64 with a corresponding threaded fastener 32 of the force gauge 30. An adjustment element 68 engages the drive portion 66 with a free end thereof abutting the end of the sliding portion 64 for adjusting the drive portion 66. A fastener 69 engages the end of the sliding portion 64 with a free end thereof abutting the drive portion 66, thereby fixing the drive portion 66 to the sliding portion 64.

Figure 3:
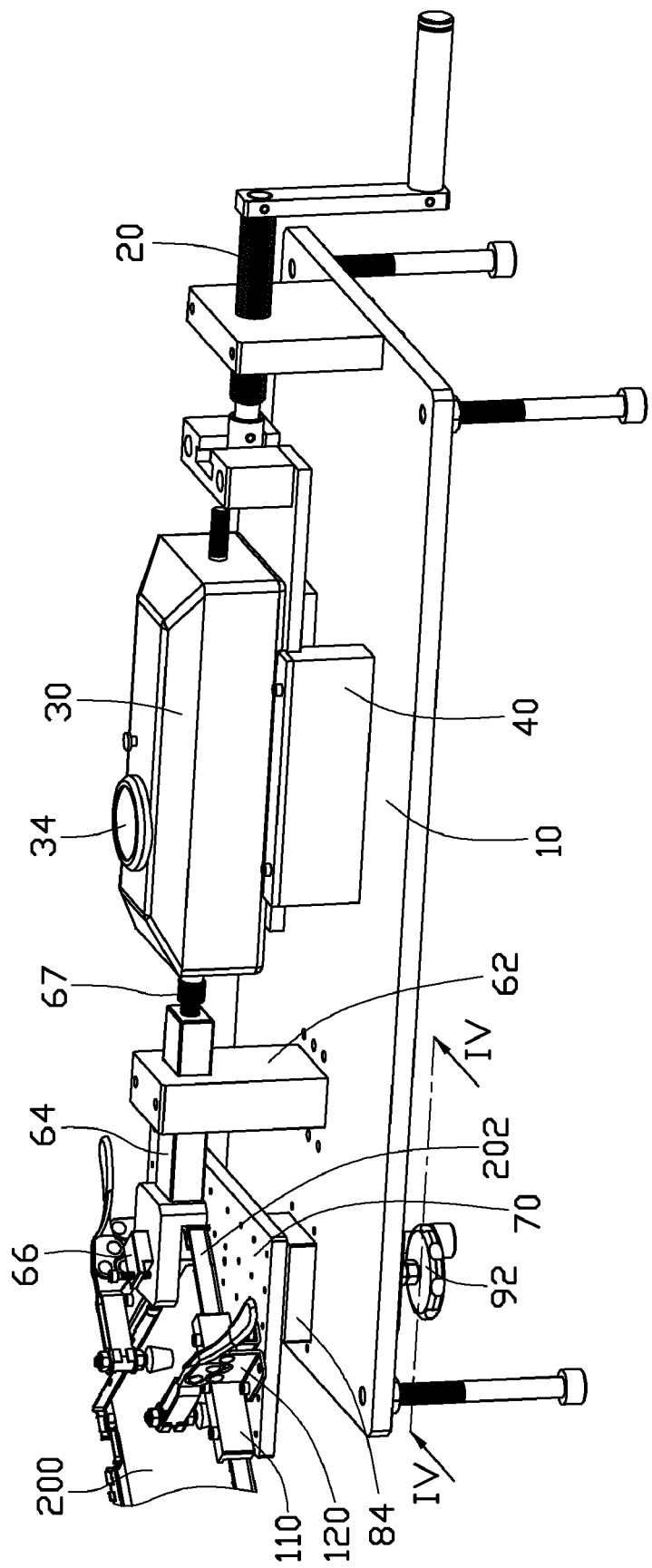
FIG. 3 is an assembled view of the apparatus of FIG. 1, during object testing.
Figure 4:
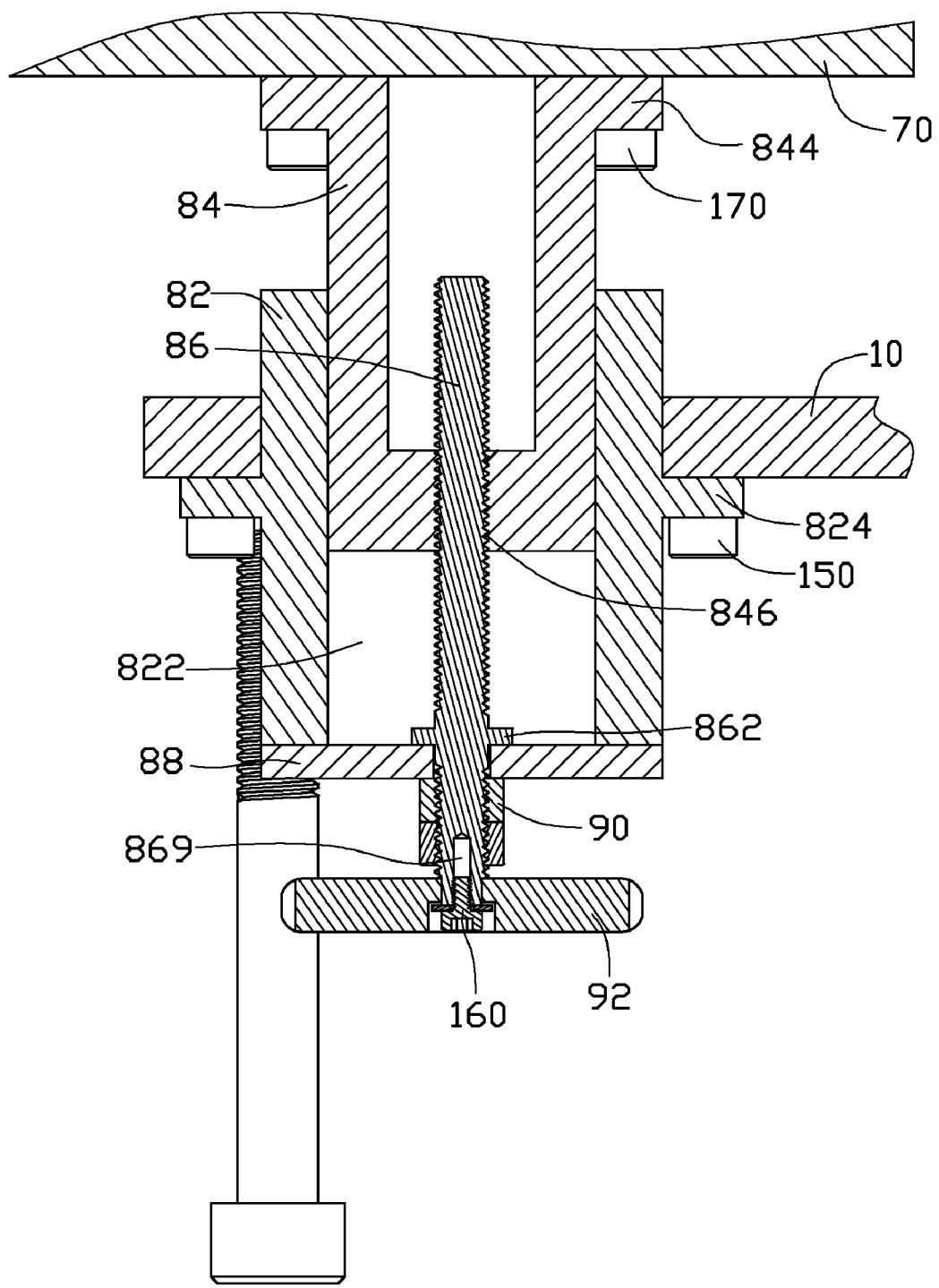
FIG. 4 is a partial, cross-section view taken along line IV-IV of FIG. 3.

Referring also to FIGS. 3 and 4, during assembly, the mounting panel 88 is fixed to the bottom surface of the pedestal 82 by a plurality of fasteners 140, thereby covering the chamber 822 of the pedestal 82 at the underside of the chamber 822. The pedestal 82, together with the mounting panel 88 are received in the opening 11 of the support platform 10 with the bulges 824 of the pedestal 82 abutting the underside of the support platform 10. The bulges 824 of the pedestal 82 are secured to the support platform 10 by a plurality of fasteners 150, thereby securing the pedestal 82 to the support platform 10. The first threaded section 864 of the adjustment rod 86 engages the threaded hole 846 of the slider 84. The sliding block 842 of the slider 84, together with the adjustment rod 86 are received into the chamber 822 of the pedestal 82. The fixing section 868 and the second threaded section 867 of the adjustment rod 86 pass through the smooth hole 882 of the mounting panel 88, and the smooth section 866 of the adjustment rod 86 is received into the smooth hole 882, thereby allowing the flange 862 of the adjustment rod 86 to abut one corresponding side of the mounting panel 88. The two circular fasteners 90 are engaged on the second threaded section 867 of the adjustment rod 86 after its passage through the fixing section 868 thereof and abutting of the other opposite side of the mounting panel 88. Thus, the adjustment rod 86 is pivotally mounted to the mounting panel 88. The fixing section 868 of the adjustment rod 86 passes through the securing hole 922 of the manipulation member 92. The manipulation member 92 is fixed to the fixing section 868 with a fastener 160 extending in the fixing hole 869 of the fixing section 868. The installation board 70 is attached to the carrier 844 of the slider 84 by a plurality of fasteners 170. The two blocking portions 110 and two clamps 120 of the clamping mechanism 100 are mounted at different positions of the installation board 70 by fasteners according to need.

During testing of an injection molded product 200 with a right-angle corner portion 202, the blocking portions 110 and clamps 120 of the clamping mechanism 100 fix the installation board 70 according to need, with outer surfaces of two adjacent sides at the corner portion 202 abutting the blocking portions 110, and the clamps 120 clamping the product 200 onto the installation board 70. Manipulation member 92 of the adjustment mechanism 80 rotates the adjustment rod 86. Thus, the smooth section 866 of the adjustment rod 86 is only rotated in the smooth hole 882 of the mounting panel 88, and does not move up and down relative to the mounting panel 88. With the first threaded section 864 of the adjustment rod 86 being rotated in the threaded hole 846 of the slider 84, the slider 84 is moved up and down relative to the pedestal 82, thereby adjusting the combined installation board 70 and product 200 up and down relative to the support platform 10, allowing the drive portion 66 of the push-pull mechanism 60 to abut opposite inner surfaces of two adjacent sides at the corner portion 202. Meanwhile, adjustment element 68 of the push-pull mechanism 60 rotates to adjust the drive portion 66 to be located in place at the corner portion 202 via the free end of the adjustment element 68 abutting the drive portion 66. After adjustment, the drive portion 66 is tightened by the free end of the fastener 69.

The force gauge 30 is moved relative to the installation mechanism 40 by pull of the drive mechanism 20. Thus, the force gauge 30 pulls the sliding portion 64 of the push-pull mechanism 60 to slide relative to the stand portion 62 by the connecting portion 67. Therefore, the drive portion 66 exerts pulling force on the inner surfaces of the two adjacent sides at the corner portion 202, causing the two adjacent sides to deform in different directions. When the reading on the dial 34 of the force gauge 30 equals or exceeds a predetermined value, the drive mechanism 20 stops pulling. In this circumstance, if the corner portion 202 dose not rupture, the product 200 passes, and if the corner portion 202 ruptures, the product 200 does not pass. The product 200 is moved up and down by the adjustment mechanism 80, which achieves high testing efficiency, and the labor intensity of the operator is eased.

In other testing, the drive portion 66 of the push-pull mechanism 60 can exert pushing force on the product 200 by driving the drive mechanism 20 in the reverse direction.

It is to be understood, however, that even though numerous characteristics and advantages of the disclosure have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An apparatus for testing strength of an object, the apparatus comprising:
    a support platform;
    a force gauge;
    an installation mechanism for slidable installation of the force gauge on the support platform;
    a drive mechanism mounted to the support platform to move the force gauge;
    a pull-push mechanism connected to the force gauge to be pushed or pulled by the force gauge and exert push or pull force on the object;
    an installation board supporting the object thereon; and
    an adjustment mechanism comprising a pedestal secured to the support platform, a slider for fixing the installation board thereon, an adjustment rod pivotally mounted to the pedestal and threaded into the slider, and a manipulation member fixed to the adjustment rod; wherein the manipulation member rotates the adjustment rod relative to the slider, thereby sliding the slider relative to the pedestal, and the installation board is moved during sliding of the slider relative to the pedestal so that the object on the installation board is adjusted relative to the support platform.

2. The apparatus of claim 1, wherein a threaded hole is defined in the slider opposite to the installation board, and the adjustment rod engages the threaded hole.

3. The apparatus of claim 2, wherein a chamber defined in the pedestal slidably receives the slider.

4. The apparatus of claim 3, wherein the chamber extends along a lengthwise direction of the pedestal between two opposite surfaces of the pedestal, a mounting panel is fixed to one of the two surfaces of the pedestal, a smooth hole is defined in the mounting panel, the adjustment rod comprises a flange abutting the mounting panel, a first threaded section extends out from a side of the flange and into the chamber of the pedestal and the threaded hole of the slider, and a smooth section extends out from an opposite side of the flange and is pivotally received in the smooth hole of the mounting panel.

5. The apparatus of claim 4, wherein the adjustment rod further comprises a second threaded section extending out from the smooth section and placed outside the mounting panel, and the adjustment mechanism further comprises at least one circular fastener engaging on the second threaded section to fix the adjustment rod to the mounting panel with the flange of the adjustment rod.

6. The apparatus of claim 5, wherein a fixing section extends out from the second threaded section of the adjustment rod, and the manipulation member has the shape of a round tray defining a securing hole in a center thereof to receive the fixing section.

7. The apparatus of claim 6, wherein a fixing hole is defined in a distal end of the fixing section, and a fastener extends in the fixing hole of the fixing section to fix the manipulation member to the fixing section.

8. The apparatus of claim 3, wherein the slider comprises a sliding block slidably received in the chamber of the pedestal, and a carrier formed on the sliding block to support the installation board.

9. The apparatus of claim 1, wherein an opening is defined in the support platform adjacent to the pull-push mechanism to receive the pedestal, two bulges protrude from the pedestal and are secured to the support platform by a plurality of fasteners, thereby securing the pedestal in the opening of the support platform.

10. The apparatus of claim 1, wherein the pull-push mechanism further comprises a stand portion fixed on the support platform, a sliding portion slidably extending through the stand portion, and a drive portion adjustably mounted to the sliding portion for exerting push or pull force on the object, and the connecting portion is connected to the sliding portion.

* * * * *